United States Patent [19]

Williams et al.

[11] Patent Number: 5,061,801

[45] Date of Patent: Oct. 29, 1991

[54] INTERMEDIATE FOR MAKING 3-OXO-4-AZA-ANDROST-1-ENE 17β-KETONES

[75] Inventors: John M. Williams, Somerset; Ulf H. Dolling, Westfield, both of N.J.

[73] Assignee: Merck & Co., Inc., Rahway, N.J.

[21] Appl. No.: 586,922

[22] Filed: Sep. 24, 1990

[51] Int. Cl.[5] .................... C07J 73/00; A61K 31/58
[52] U.S. Cl. .................... 546/77; 514/284; 514/859
[58] Field of Search ............... 546/77; 514/284, 859

[56] References Cited

U.S. PATENT DOCUMENTS

| | | | |
|---|---|---|---|
| 4,220,775 | 9/1980 | Rasmusson et al. | 514/859 |
| 4,377,584 | 3/1983 | Rasmusson et al. | 514/859 |
| 4,760,071 | 7/1988 | Rasmusson et al. | 514/284 |
| 4,859,681 | 8/1989 | Rasmusson et al. | 514/284 |

OTHER PUBLICATIONS

J. Med. Chem., 1986, vol. 29, pp. 2298–2315, by R. H. Rasmusson, et al.
J. Chem. Society, 1954, pp. 1188–1190, by H. Bassett.
Tetrahedron Letters, vol. 22, No. 39, pp. 3815–3818, 1981, by S. Nakin, et al.

*Primary Examiner*—Mukund J. Shah
*Assistant Examiner*—Yogendra N. Gupta
*Attorney, Agent, or Firm*—Salvatore C. Mitri; Charles M. Caruso

[57] ABSTRACT

Described is a new intermediate and new process for preparing 3-oxo-4-aza-androst-1-ene 17β-ketones. The process involves converting the corresponding 17β-alkyl carboxylate to the N-methoxy-N-methyl carboxamide and reacting this with an appropriate Grignard reagent to form the desired ketone. The reaction can be conducted in "one pot", thus eliminating isolation of intermediates and avoiding the use of less stable intermediates, e.g., acid chlorides, acyl imidazolides and the like. The intermediate has the formula:

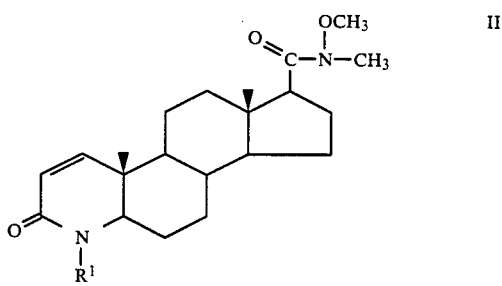

wherein
$R^1$ is hydrogen.

2 Claims, No Drawings

INTERMEDIATE FOR MAKING 3-OXO-4-AZA-ANDROST-1-ENE 17β-KETONES

BACKGROUND OF THE INVENTION

This invention is concerned with a new intermediate and process for preparing 17β-acylsubstituted 3-oxo-4-azasteroids by utilizing a 17β-N-methoxy-N-methyl carboxamide as a common intermediate.

Processes for making 17β-acyl-substituted 3-oxo-4-azasteroids are known in the art. For example, European Patent Application 85301122.9 discusses the synthesis of 17β-acyl-substituted 3-oxo-4-azasteroids involving the formation of a 17β-(2-pyridylthiocarbonyl)-3-oxo-4-aza steroid which can be substituted at the 4-position and can have a double bond at the 1,2-positions. This compound is then reacted with a Grignard reagent to form a 17β-acyl-3-oxo-4-aza steroid. While this process is practical for small scale preparations, it has the disadvantage of requiring extensive chromatography to obtain the final product.

Rasmusson et. al., J. Med. Chem. 1986, 29, 2298–2315 and U.S. Pat. Nos. 4,220,775 and 4,377,584 also discuss the synthesis of 17β-substituted 3-oxo-4-azasteroids involving the use of a very reactive 17β-imidazolide intermediate in a Grignard reaction. Extensive chromatography is also required here.

Other methods are known for producing 17β-acyl androstenones and involve reacting a 17β-carboxylic acid ester with Grignard reagents, e.g. phenylmagnesium bromide to form the 17β-acyl analog. However, a serious side reaction occurs wherein the product 17β-acyl compound formed by the Grignard Reaction, can undergo further reaction with the Grignard reagent to produce the diphenyl carbinol, e.g., see Compound 4 in Scheme 1, compromising yield and purity of the desired ketone.

What is desired in the art is an 17β-substituted androstenone intermediate which is stable and which can undergo reaction with a Grignard reagent to produce 17β-acyl androstenones in high yield and purity.

SUMMARY OF THE INVENTION

We have found that the problems of the prior art in forming 17β-acyl androstenone derivatives via the Grignard reaction can be overcome by utilizing a N-methoxy-N-methyl carboxamide as an intermediate.

By this invention there is provided a compound of the formula:

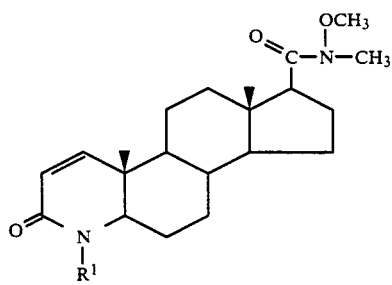

II wherein
$R^1$ is hydrogen.

Further provided is a method for preparing a compound of the formula:

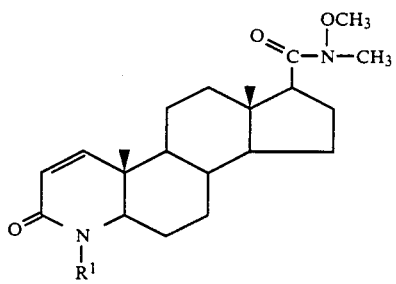

II wherein
$R^1$ is hydrogen; which process comprises reacting a compound of the formula:

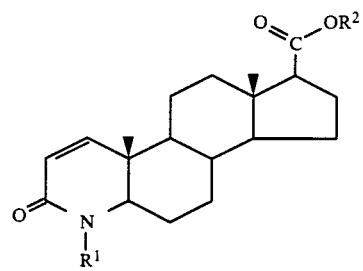

I wherein
$R^2$ is $C_1$–$C_4$ alkyl; with N,O-dimethylhydroxylamine and RMgX in a dry inert organic solvent, in a dry atmosphere, at a temperature of 0° to 25° C., for a sufficient time to form the amide II.

The disclosed intermediate is useful in a new process for preparing a compound of the formula

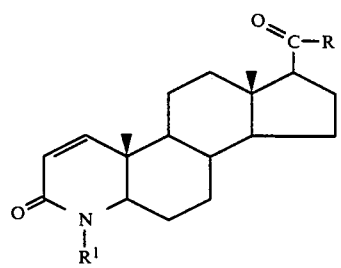

III wherein
R is
  (i) a $C_1$–$C_{12}$ straight or branched chain alkyl group;
  (ii) a $C_3$–$C_8$ cycloalkyl group, or
  (iii) $C_6$–$C_{12}$ aryl; wherein the above groups of (i), (ii), (iii) can be substituted with $C_1$–$C_4$ linear/branched alkyl; $C_1$–$C_4$ linear/branched alkoxy; protected hydroxy; or fluoro; and
$R_1$ is hydrogen;
which comprises reacting an amide of the formula:

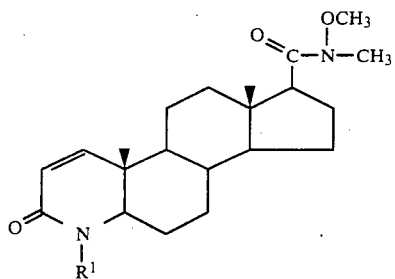

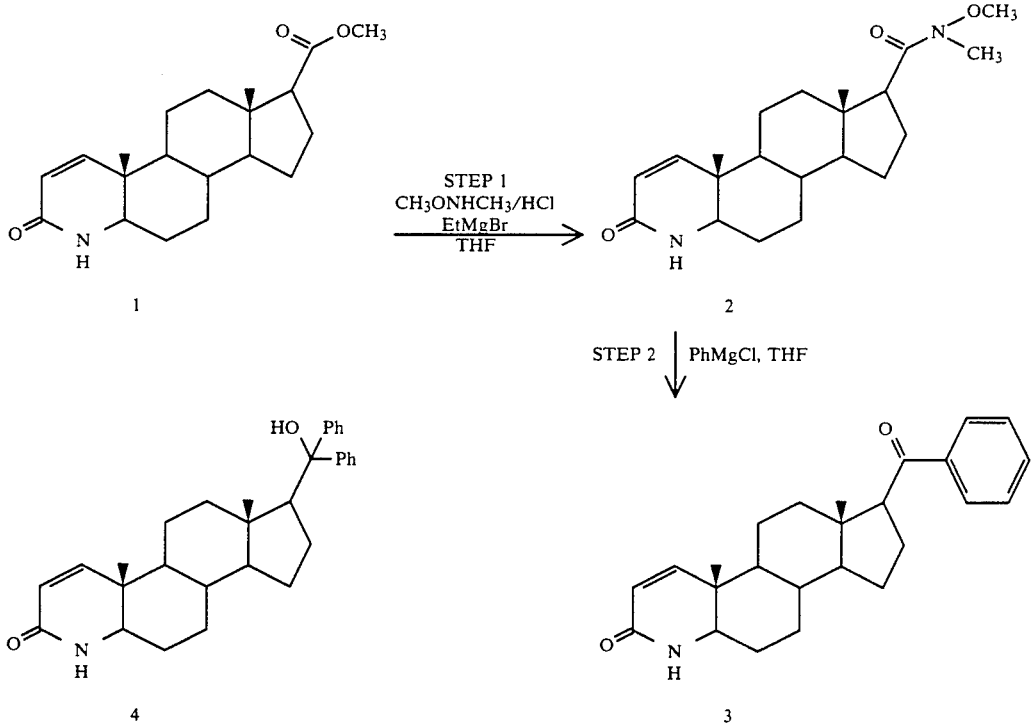

SCHEME 1 wherein
R¹ is as previously defined, with a compound of the formula RMgX,
wherein
R is as previously defined, and
X is a halogen selected from the group consisting of chlorine, bromine and iodine, in a dry, inert organic solvent at a temperature in the range of 0° to 65° C., under an inert atmosphere, for a sufficient time to form II.

The azasteroid compounds prepared by the processes of the present invention are testosterone 5α-reductase inhibitors useful for treating the hyperandrogenic conditions of acne vulgaris, seborrhea, female hirsutism, androgenic alopecia, including male pattern alopecia, prostatic carcinoma and benign prostatic hypertrophy by topical or systemic administration.

DETAILED DESCRIPTION OF THE INVENTION

The process of the instant invention can be seen and understood by reference to the following Scheme 1.

Starting Compound 1, being the known methyl 3-oxo-4-aza-5-α-androst-1-ene-17β-carboxylate (Δ¹-aza ester) is reacted with a N,O-dimethylhydroxylamido magnesium bromide prepared from e.g., N,O-dimethylhydroxylamine hydrochloride, and a Grignard reagent, e.g., ethylmagnesium bromide, in a dry, inert solvent, e.g. tetrahydrofuran, at a temperature of 0° to 25° C., e.g., under nitrogen.

The in situ formed Grignard reagent is used in an amount of about 1.9 to 1 moles per mole of the N,O-dimethylhydroxylamine salt. The molar ratio of the N,O-dimethylhydroxylamine salt to the Δ¹-aza ester used is about 4.5:1.

The solvent for this reaction is a dry inert organic solvent including $C_4$-$C_5$ linear or cyclic ethers, e.g., dimethoxyethane, diethyl ether, methyl t-butyl ether, tetrahydrofuran (THF), dioxane, and the like.

Time for the completed reaction is about 1-4 hours and the product 17β N-methoxy-N-methyl carboxamide, Compound 2, can be isolated and purified by conventional methods including quenching by the addition of ammonium chloride, followed by treatment with activated carbon to remove impurities and recrystallization, e.g. from acetic acid/water. Yields are in the range of 85 to 95% based on reacting Δ¹-aza ester.

Preferably, the carboxamide 2 is not isolated but used in the subsequent Grignard reaction in the same reaction vessel.

Step 2, the Grignard reaction with RMgX, as defined above, is carried out in a solvent which is the same as described in the previous step, at a temperature in the range of 0° to 65° C., preferably 20° C., in an inert atmosphere, e.g. dry nitrogen, wherein a molar ratio of Grignard reagent to the carboxamide of about 7.5:1 is used. The Grignard reagent is preferably added to the carboxamide 2 in the solvent, under agitation, under dry conditions, and after addition allowed to stir for 6 to 12 hours. Workup of the reaction mixture is conventional and can include the addition of 0.5N HCl followed by isolation and recrystallization from, e.g. acetic acid/water. Yields in the process are in the range of 80-95% based on the starting carboxamide.

The Grignard reagent contains R which is described above and which representative examples include interalia: methyl, ethyl, n-propyl, n-butyl, n-pentyl, t-hexyl, t-heptyl, iso-octyl, sec-octyl, n-nonyl, t-decyl, n-undecyl, n-dodecyl, cyclopropyl, cyclobutyl, cyclopentyl, cyclohexyl; phenyl, meta and para substituted phenyl, naphthyl, biphenyl; wherein the above groups can be substituted by $C_1$-$C_4$ linear or branched alkyl, e.g., methyl, ethyl, isopropyl, t-butyl, $C_1$-$C_4$ alkoxy, e.g. methoxy, ethoxy, isopropoxy, sec-butoxy, or fluoro. Where the substituent is protected hydroxy, a protecting group is utilized to protect the hydroxy group during the Grignard reaction, for example, where R is protected para-hydroxyphenyl, this Grignard reagent can be derived by starting with an appropriate bromophenol, protecting the phenolic —OH with a conventional protecting group, which is unreactive during the Grignard reaction, e.g. trioganosilyl, i.e. t-butyldimethylsilyl, carrying out the Grignard reaction and then deblocking the silyl group by the use of, e.g. refluxing aqueous tetrabutylammonium fluoride. The reactant Grignard reagents in the invention can be made by conventional methods in the art.

The method of preparing the novel 17$\beta$-acyl compounds of the present invention, already described above in general terms, may be further illustrated by the following examples, which should not be construed as limiting the scope or spirit of the instant invention.

EXAMPLE 1

(5$\alpha$,17$\beta$)-N-Methoxy-N-methyl-3-oxo-4-aza-androst-1-ene-17$\beta$-carboxamide (2)

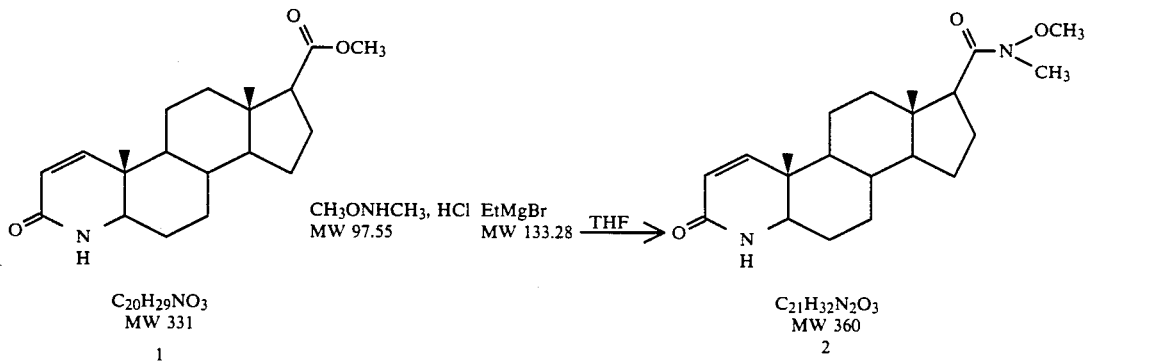

A 2 L three-neck flask equipped with an overhead stirrer, nitrogen inlet, internal thermometer, and/dropping funnel was charged with 800 mL of sieve-dried tetrahydrofuran, 19.72 g (59.6 mmol) of $\Delta^1$-aza ester (Compound 1) (for synthesis, see Rasmusson Johnston and Arth. U.S. Pat. No. 4,377,584, Mar. 22, 1983.) and 25.6 g (262.4 mmole) of N,O-dimethylhydroxylamine hydrochloride. The resulting slurry was cooled to 0° to 5° C.

A warm solution (30°-40° C.) of ethylmagnesium bromide in dry tetrahydrofuran (252 mL, 2.0 Molar, 504 mmole) was added over fifteen minutes. The pot temperature was maintained at 0°-5° C. during the addition. The reaction mixture was warmed to 25° C. over thirty minutes and aged at 22°-25° C. for one hour. The reaction was cooled to 0°-5° C. and quenched into 650 mL of 25 wt % aqueous ammonium chloride. The mixture was warmed to 40°-45° C. and the layers were separated. The organic solution was cooled to 25° C. and treated with activated carbon.

The THF solution after filtration was concentrated by atmospheric distillation to 200 mL. The resulting slurry was cooled to 35° C. and 1 L of water was added over one hour. The slurry was cooled to 25° C. and aged for 2 hours. The amide was collected by filtration and washed with 200 mL of water then dried at 80° C./house vacuum to yield 19.6 g (91.4%) of amide 2 (98.8 area % pure by LC).

HPLC Conditions:
Column: Zorbax phenyl 25 cm×4.6 mm.
Temp: 22° C.
Detector: UV @ 210 nm.
Eluent: 40% $CH_3CN$/60% $H_2O$ (0.1% $H_3PO_4$)
Flow Rate: 2 mL/min.
Retention Time: $\Delta^1$-aza ester (I) 10.95 min. Amide (2) 5.42 min.

EXAMPLE 2

17$\beta$-Benzoyl-4-aza-5$\alpha$-androst-1-ene-3-one (3)

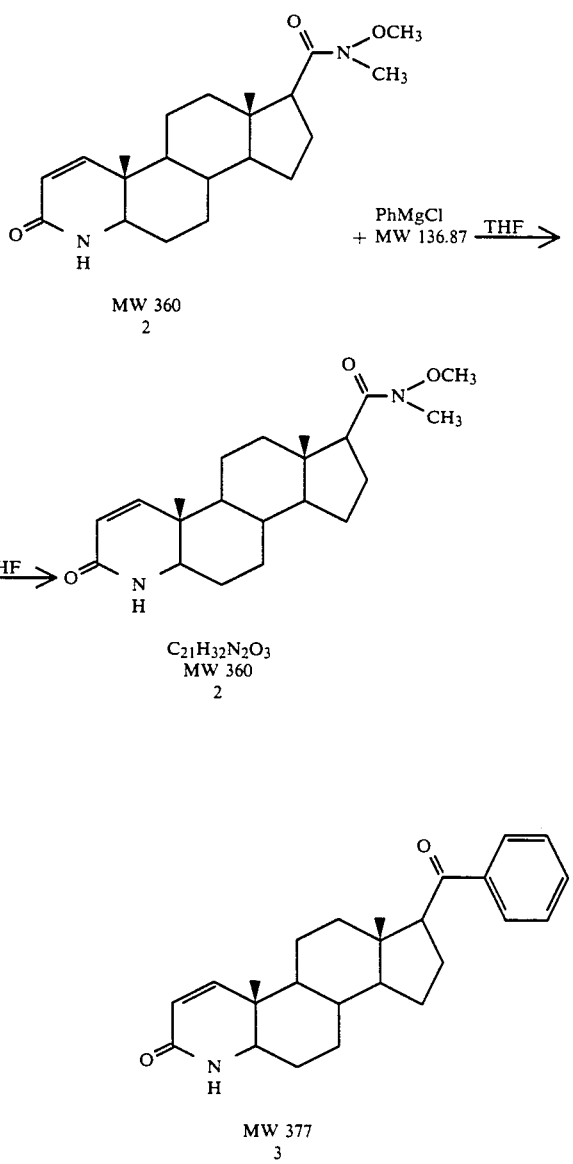

A 1 L three-neck flask equipped with an overhead stirrer, N₂ inlet, internal thermometer and dropping funnel was charged with 400 mL of sievedried tetrahydrofuran and 10.0 g (27.8 mmole) of amide 2 (98.8 area % pure by LC). The resulting slurry was cooled to 0°-5° C. A solution of phenylmagnesium chloride in tetrahydrofuran (104 mL, 2M, 208 mmole) was added over fifteen minutes while maintaining a temperature of 0°-5° C. The reaction mixture was warmed to 25° C. aged at 22°-25° C. for 7 hours, then cooled to 0°-5° C., and quenched into a mixture of 500 mL of 25 wt % aqueous ammonium chloride and 400 mL of THF (cooled to 5°-10° C.). The quench mixture was warmed to 40°-45° C. and aged for thirty minutes. After one hour settling at 40°-45° C. the bottom aqueous layer was cut. The THF solution (890 mL) contained 11.1 mg/mL of 3 by LC assay (9.9 g, 94.5% yield). The THF solution was concentrated by atmospheric distillation to 200 mL. The resulting slurry was cooled to 25° C. and 10 mL of isopropyl acetate was added. At 25° C. 200 mL of 0.5N HCl was added to the slurry. The three-phase mixture was filtered and the cake was washed with 50 mL of isopropyl acetate (25° C.). The solid batch was dried at 80° C. under vacuum to yield 9.06 g (86.5%), 99.2 area % pure by LC, of phenyl ketone 3.

Ten grams of crude phenyl ketone 3 was dissolved in 1 L of glacial acetic acid at 20°-25° C., 110 mL of water was added and the clear solution aged at 22°-25° C. for 7 hours. The clear solution was filtered into 1 L of water with vigorous stirring over one hour, and the resulting slurry was aged at 22°-25° C. for two hours. The product was collected by filtration and washed with 200 mL of water, then vacuum dried at 80° C. to yield 9.6 g (96%) of pure phenyl ketone (3) as a white crystalline solid.

HPLC Conditions: Assay of the Reaction Mixture
Column: Zorbax phenyl, 25 cm×4.6 mm.
Temp: 22° C.
Detector: UV @ 210 mm
Eluant: 50% CH₃CN/50% H₂O (0.1% H₃PO₄)
Flow rate: 2 mL/min
Retention time in mins:
 Amide 2: 3.31
 Ketone 3: 9.82
 Tert alcohol 4: 22.40.

HPLC Conditions: Assay of the Reaction Mixture
Column: Dual Zorbax Rx 25 cm×4.6 mm.
Temp: 22° C.
Detector: UV @ 210 mm.
Eluant: 50% CH₃CN/50% H₂O (0.1% H₃PO₄).
Flow rate: 2 mL/min.
Retention time in mins:
 Amide 2: 3.31
 Ketone 3: 9.82
 Tert alcohol 4: 22.40.

Analytical Data: Micro analysis calc'd for C₂₅H₃₁NO₂ (MW 377) C, 79.6; N, 3.70; H, 8.19 Found: C, 79.67, N, 3.70; H, 8.19. LC: 99.7 area %, 3 impurities each <0.5%. MP: 307° C. (dec.),

EXAMPLE 3

"One-Pot" Procedure

The two reactions described in Example 1 and 2 can be conducted as a "one-pot" procedure. The Δ¹-aza ester (I) is reacted with N-methoxy-N-methyl amido magnesium bromide as described in Example 1. Following completion of the reaction, the mixture is refluxed for zh, cooled to 0° C., and 7.5 molar equivalents of phenylmagnesium bromide are added. Warming to 25° C. and stirring for 6 hours provides a 70% assay yield of the phenyl ketone.

What is claimed is:

1. A method for preparing a compound of the formula:

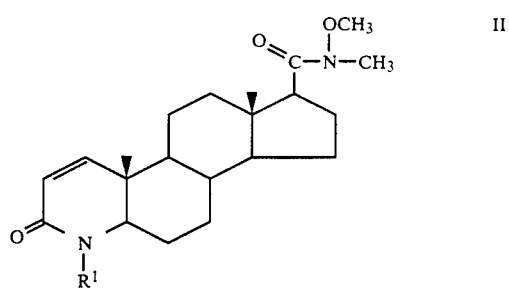

wherein
R¹ is hydrogen; which process comprises reacting a compound of the formula

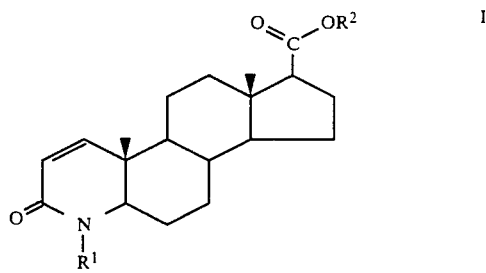

wherein
R² is C₁-C₄ alkyl; with N,O-dimethylhydroxylamine and RMgX in a dry inert organic solvent, in dry atmosphere, at a temperature of 0° to 25° C., for a sufficient time to form the amide II.

2. A compound of the formula

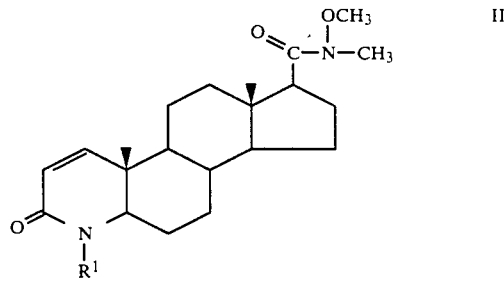

wherein
R¹ is hydrogen.

* * * * *